United States Patent
Ognibene et al.

(10) Patent No.: US 11,040,012 B2
(45) Date of Patent: Jun. 22, 2021

(54) PULVERULENT, DIRECTLY COMPRESSIBLE POLYVINYL ALCOHOL GRADES

(71) Applicant: Merck Patent GmbH, Darmstadt (DE)

(72) Inventors: Roberto Ognibene, Darmstadt (DE); Finn Bauer, Bensheim (DE); Thorsten Wedel, Stockstadt/Rhein (DE); Guenter Moddelmog, Reinheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/500,245

(22) PCT Filed: Jul. 3, 2015

(86) PCT No.: PCT/EP2015/001357
§ 371 (c)(1),
(2) Date: Jan. 30, 2017

(87) PCT Pub. No.: WO2016/015814
PCT Pub. Date: Feb. 4, 2016

(65) Prior Publication Data
US 2018/0207101 A1    Jul. 26, 2018

(30) Foreign Application Priority Data

Jul. 30, 2014  (EP) .................................. 14002664

(51) Int. Cl.
*A61K 9/20*   (2006.01)

(52) U.S. Cl.
CPC .......... *A61K 9/2027* (2013.01); *A61K 9/2054* (2013.01); *A61K 9/2095* (2013.01)

(58) Field of Classification Search
CPC ... A61K 9/2027; A61K 9/2054; A61K 9/2095
See application file for complete search history.

(56) References Cited

U.S. PATENT DOCUMENTS

| 4,990,335 A | * | 2/1991 | Bateman | A61K 9/2027 |
| | | | | 424/408 |
| 5,733,578 A | | 3/1998 | Hunter et al. | |
| 2003/0180360 A1 | * | 9/2003 | Am Ende | A61K 9/2009 |
| | | | | 424/468 |
| 2006/0039967 A1 | | 2/2006 | Ohta et al. | |
| 2006/0177380 A1 | * | 8/2006 | Emigh | A61K 9/0043 |
| | | | | 424/10.1 |
| 2006/0204574 A1 | | 9/2006 | Ogawa et al. | |
| 2007/0020335 A1 | | 1/2007 | Chen et al. | |
| 2008/0020055 A1 | | 1/2008 | Monteith et al. | |
| 2008/0138404 A1 | | 6/2008 | Walsh et al. | |
| 2008/0305165 A1 | | 12/2008 | Noh et al. | |
| 2017/0209377 A1 | * | 7/2017 | Furo | A61K 47/32 |

FOREIGN PATENT DOCUMENTS

| CN | 101257894 A | 9/2008 | |
| CN | 101374505 B | 7/2013 | |
| CN | 101495100 B | 9/2014 | |
| JP | H02502720 A | 8/1990 | |
| JP | 2011148832 A | 8/2011 | |
| JP | 2013087074 A | * | 5/2013 |
| JP | 2013087074 A | | 5/2013 |
| WO | 88/07366 A1 | 10/1988 | |
| WO | 97/17947 A1 | 5/1997 | |
| WO | WO-2008020990 A1 | * | 2/2008 ........... A61K 9/2054 |
| WO | 16013675 A1 | 1/2016 | |

OTHER PUBLICATIONS

Kuraray, PVA Standard, 2014 (Year: 2014).*
DiNunzio, Drug Development and Industrial Pharmacy, 38, 2, 2012 (Year: 2012).*
International Search Report dated Aug. 10, 2015, issued in corresponding PCT/EP2015/001357, 2 pages.

* cited by examiner

*Primary Examiner* — Robert A Wax
*Assistant Examiner* — William Craigo
(74) *Attorney, Agent, or Firm* — Millen White Zelano and Branigan, PC; Csaba Henter

(57) ABSTRACT

The present invention relates to premixes for the production of active compound-containing tablets which comprise polyvinyl alcohols (PVAs). The invention also relates to active compound-containing tablets which comprise a corresponding premix.

19 Claims, 1 Drawing Sheet

PULVERULENT, DIRECTLY COMPRESSIBLE POLYVINYL ALCOHOL GRADES

The present invention relates to premixes for the production of active compound-containing tablets which comprise polyvinyl alcohols (PVAs). The invention also relates to active compound-containing tablets which comprise a corresponding premix.

PRIOR ART

Polyvinyl alcohols (PVAs) are synthetic polymers which are available in various grades, in particular with respect to degree of polymerisation and viscosity. Polyvinyl alcohols (PVAs) are basically synthetic, flexible polymers which are obtained by alkaline hydrolysis of polyvinyl acetate. Polyvinyl acetate is in turn obtained by free-radical polymerisation from vinyl acetate. Through different chain lengths and different degrees of hydrolysis of the polyvinyl acetates, polyvinyl alcohols (PVAs) having a very wide variety of physical properties can be obtained. The PVAs are employed, in particular, as film formers, adhesive gels and as viscosity modulator, in a multiplicity of areas of application, for example paints, papers, textiles, cosmetics and in pharmaceuticals, including drug delivery systems, etc.

Of particular interest for the pharmaceutical industry is the use of PVAs in pharmaceutical preparations, such as, for example, in ophthalmic preparations, as film formers for coated tablets, as binders in granules or as coating component in plasters, and also in drug delivery systems. Of very particular interest is the use of various PVA grades in the formulation of solid oral pharmaceutical administration forms having extended release of active compound, for example in so-called "retard tablets". In these tablets, the active compound is in finely divided form in a PVA matrix. Delayed release of active compound is achieved in polymer-containing pharmaceutical formulations of this type through the tablets not dissolving directly in the presence of liquid, such as in the mouth or gastrointestinal tract, but instead swelling and the active compound only being released little by little by diffusion.

Galenically modified tablets of this type enable the active compound to be released from the administration form in a controlled manner over an extended time in the body, in order thus to maintain a therapeutically effective blood level of the medicament over an extended period (several hours). The two essential advantages of such retarded formulations are—in contrast to tablets having immediate release of active compound after taking—firstly the avoidance of undesired and possibly also toxic blood/plasma levels of the API and also a reduction in the frequency with which the tablets are taken (for example only once/daily instead of 3 times/daily) and thus an improvement in so-called patient compliance together with an improved therapeutic result of the medicinal treatment.

Known polyvinyl alcohols which are specified for use in pharmaceutical formulations according to the various pharmacopoeias (Pharmacopoea Europaea, Ph. Eur.; United States Pharmacopoeia (USP), and the Japanese Pharmacopoeia (JP or JPE), but cannot be tableted directly by the action of pressure or only under particular conditions. A particular problem in this connection thus consists in the production in a simple manner of tablets which principally consist of corresponding PVAs as active compound excipient in which the active compound is homogeneously distributed. Direct tabletability of PVA-containing formulations usually has to be achieved in the presence of relatively high proportions of further binders, such as lactose, and of lubricants and possibly further additives. Formulations in which PVAs are employed as active compound excipient are frequently prepared in the presence of aqueous or alcoholic solutions. For example, it is known to produce corresponding tablets having extended release of active compound by compressing the active compound and PVA in the presence of further additives after wet granulation. The latter is associated with the disadvantage that the requisite solvents have to be removed again with input of energy.

OBJECT

As arises from the above-said, it is desirable to prepare a directly compressible mixture for a tableting matrix based on polyvinyl alcohols which can be employed for the preparation of formulations, in particular of tablets, having delayed release of active compound. The object of the present invention is thus also to provide polyvinyl alcohol-containing tablets having delayed release of active compound.

The use of a combination of fine-grained, optionally ground, polyvinyl alcohols which per se have only low compressibility with microcrystalline celluloses surprisingly now gives a directly compressible mixture as tableting matrix which can be used for the preparation of formulations having delayed release of active compound.

BRIEF DESCRIPTION OF THE INVENTION

The present invention provides the pharmaceutical formulation scientist with a premix for the production of active compound-containing tablets which comprises a co-mixture of polyvinyl alcohols (PVAs) which have average particle sizes <100 µm and microcrystalline celluloses (MCCs). The present invention preferably relates to premixes of this type which comprise microcrystalline celluloses having an average particle size of 150 µm, preferably having an average particle size in the range from 100 µm to 140 µm. Particularly good properties are possessed by directly compressible premixes which comprise polyvinyl alcohols having an average particle size in the range from 80 µm to 90 µm, so that the object of the present invention is achieved, in particular, by corresponding directly compressible co-mixtures. In accordance with the invention, the premixes are co-mixtures of PVA with microcrystalline celluloses in the weight ratio 2:1 to 1:2, preferably in a ratio of 2:1 to 1:1. In accordance with the invention, the premixes are co-mixtures of microcrystalline celluloses (MCCs) and polyvinyl alcohols (PVAs) which are suitable for active compound retardation, where the latter meet the requirements of the pharmacopoeias (Ph. Eur., USP/NF and JPE. Premixes according to the invention in the form of co-mixtures comprise microcrystalline celluloses (MCCs) and polyvinyl alcohols (PVAs) of grades 18-88, 26-88 and 40-88 which are suitable for active compound retardation in accordance with the requirements of the pharmacopoeias Ph. Eur., USP/NF and JPE, and of grade 28-99 and of grade 20-99 in accordance with the requirements of JPE and Ph. Eur. These co-mixtures preferably consist of microcrystalline celluloses (MCCs) and polyvinyl alcohols (PVAs) of grades PVA 26-88 and PVA 40-88 which are suitable for active compound retardation. Corresponding premixes can be shaped by compression at a pressing force of 20 kN to give tablets having hardnesses of >380 N, which and a friability of ≤0.1% by weight.

Tablets having hardnesses of >178 N which have a friability ≤0.1% by weight can be shaped by compression at a pressing force of 10 kN.

However, the present invention also relates to active compound-containing tablets which comprise a carrier matrix consisting of polyvinyl alcohols and microcrystalline celluloses. Particularly good properties are exhibited by corresponding tablets having extended release of active compound which comprise such a premix of microcrystalline celluloses (MCCs) and polyvinyl alcohols (PVAs), as characterised above, in an amount of 1-99% by weight, preferably in an amount of 5-95% by weight, very particularly preferably in an amount of 10-90% by weight, based on the total weight of the tablet. Active compound-containing tablets can advantageously be obtained from the premixes according to the invention by compression at low pressing forces, where the tablets which have high tablet hardnesses require low ejection forces. Corresponding active compound-containing tablets having hardnesses of >380 N and a friability ≤0.1% by weight can be obtained from the premixes according to the invention by compression at a pressing force of 20 kN, or tablets having hardnesses of >178 N and a friability ≤0.1% by weight can be obtained at a pressing force of 10 kN. In particular, the present invention relates to active compound-containing tablets having delayed release of active compound which comprise on the one hand the premixes described above and active compounds from BCS class I, either alone or in combination with other active compounds.

DETAILED DESCRIPTION OF THE INVENTION

Surprisingly, the use of a combination of fine-grained, optionally ground, polyvinyl alcohols, which per se have only low compressibility, with microcrystalline celluloses now gives a directly compressible mixture as tableting matrix which can be used for the preparation of formulations having delayed release of active compound. The use of fine-grained PVAs as retardation matrices is particularly desired for the pharmaceutical formulation scientist since the fine-grained nature enables the preparation of more homogeneous mixtures with the active compound to be retarded. Homogeneous mixtures in turn are important for the individual dosage accuracy ("content uniformity"), i.e. they are important for the distribution of the same amount of active compound in each individual tablet. In addition, fine-grained PVA particles and consequently large particle surface areas result in more homogeneous gel-layer formation on use in a tablet after moistening of the tablets in the gastrointestinal tract, enabling more reproducible and possibly also extended diffusion of the active compound through this gel to be achieved.

Experiments have shown that the direct-compression properties of materials are dependent, in particular, on their particle properties. Besides the particle morphology and the brittleness, a crucial role is played in this connection by, in particular, the particle size. It has been found here that the particle size of the retardation matrices based on PVA is of particular importance, more precisely the homogeneity of the active-compound distribution in the matrix, and the retardation effect, but, in particular, also the compressibility of the matrix, is influenced.

In order to investigate the influence of the particle-size distribution and to determine particularly advantageous average particle sizes, the pharmacologically certified polyvinyl grades PVA 26-88 and 40-88 were cold-ground under various conditions to give 3 fractions each with different particle sizes/particle-size distributions (fraction 1: 85-89 μm; fraction 2: 116-129 μm and fraction 3: 207-245 μm). These ground fractions were subjected to compressibility tests in combination with three commercially available microcrystalline cellulose grades of different average particle size (Vivapur® 105: ~25 μm; Vivapur® 102: ~100 μm and Vivapur® 200: ~250 μm).

The investigations surprisingly showed that none of the PVA particle fractions can be tableted in combination with a fine-grained MCC grade (~25 μm) owing to the very poor flow behaviour. On use of MCC grades having an average particle size of 100 μm or 250 μm, tablets having good hardnesses and low abrasion can be obtained with adequate flowability.

The experiments with grades PVA 26-88 and PVA 40-88 showed that harder tablets are obtained, the finer the PVA powders have been ground.

For example, in the experiments with mixtures of the two fine powder fractions PVA 26-88 and PVA 40-88 (85-89 μm) with Vivapur® 102 (~100 μm), the highest tablet hardnesses of significantly higher than 500 N are obtained at a pressing force of 30 kN. By contrast, on use of the coarser PVA fractions, i.e. powders having average particle sizes of 116-129 μm, or of 207-245 μm, significantly softer tablets are obtained. Thus, tablets having a hardness of <300 N are obtained at a pressing force of 30 kN on use of PVA 40-88 having a particle-size fraction in the range 207-245 μm if the microcrystalline cellulose Vivapur® 200 having an average particle size of ~250 μm is used. Corresponding results are shown below in compressibility diagrams.

In particular, it has been found that combinations with the commercially available microcrystalline cellulose Vivapur® 102 having an average particle size of ~100 μm tend to have better compressibility than mixtures with Vivapur® 200 having an average particle size of ~100 μm~250 μm.

As the experiments show, the particularly good compression properties of a polyvinyl alcohol having average particle sizes <90 μm, preferably in the range from 80 to 90 μm, provide the pharmaceutical formulation scientist with polyvinyl alcohols which can be employed, without prior granulation, in a direct-compression process for the production of tablets and by means of which retard tablets having optimal pharmaceutical formulation properties are obtained. In particular, these pretreated PVAs enable tablets having high hardness and low friability to be obtained. These tablet properties are particularly advantageous during further handling of the tablets, such as optionally desired colouring in rotating coating equipment, but in particular during packing in blisters, filling and transport, but also on use by the patient, for example when pressing the tablets out of the blister packs.

The conditions for the production of specific PVA particle-size fractions of this type and their particularly good compressibilities arise from the examples given below.

BRIEF DESCRIPTION OF DRAWINGS

FIG. 1 and FIG. 2 show characterisations of the various polyvinyl alcohols PVA 26-88 and 40-88 having different particle sizes mixed with MCC and Parteck LUB MST by plotting of pressing force against tablet hardness.

EXAMPLES

Figure 1:
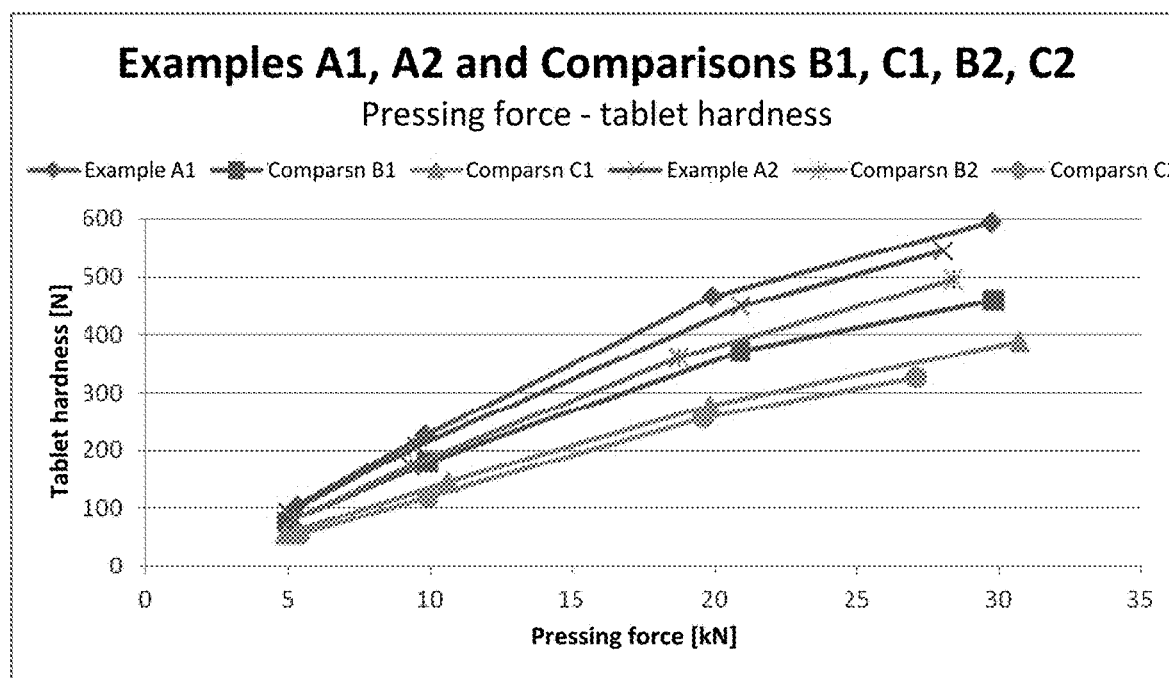
FIG. 1 and FIG. 2.

The present description enables the person skilled in the art to apply the invention comprehensively. Even without further comments, it is therefore assumed that a person skilled in the art will be able to utilise the above description in the broadest scope.

If anything is unclear, it goes without saying that cited publications and possibly cited patent literature should be consulted. Accordingly, these documents are regarded as part of the disclosure content of the present description.

For better understanding of the invention and in order to illustrate it, examples are given below which are within the scope of protection of the present invention. These examples also serve to illustrate possible variants. Owing to the general validity of the inventive principle described, however, the examples are not suitable for reducing the scope of protection of the present application to these alone.

Furthermore, it goes without saying to the person skilled in the art that, both in the examples given and also in the remainder of the description, the component amounts present in the compositions always only add up to 100% by weight or mol-%, based on the composition as a whole, and cannot exceed this, even if higher values could arise from the percent ranges indicated. Unless indicated otherwise, % data are thus regarded as % by weight or mol-%, with the exception of ratios, which are reproduced in volume figures.

The temperatures given in the examples and the description as well as in the claims are in ° C.

Equipment/Methods for Characterisation of the Substance Properties
1. Bulk density: in accordance with DIN EN ISO 60: 1999 (German version)—quoted in "g/ml"
2. Tapped density: in accordance with DIN EN ISO 787-11: 1995 (German version)—quoted in "g/ml"
3. Angle of repose: in accordance with DIN ISO 4324: 1983 (German version)—quoted in "degrees"
4. Surface area determined in accordance with BET: evaluation and procedure in accordance with the literature "BET Surface Area by Nitrogen Absorption" by S. Brunauer et al. (Journal of American Chemical Society, 60, 9, 1983) instrument: ASAP 2420 Micromeritics Instrument Corporation (USA); nitrogen; sample weight: about 3.0000 g; heating: 50° C. (5 h); heating rate 3 K/min; quoting of the arithmetic mean from three determinations
5. Particle size determination by laser diffraction with dry dispersal: Master-sizer 2000 with Scirocco 2000 dispersion unit (Malvern Instruments Ltd. UK), determinations at a counterpressure of 1 and 2 bar; Fraunhofer evaluation; dispersant RI: 1.000, obscuration limits: 0.0-10.0%, tray type: general purpose, background time: 7500 msec, measurement time: 7500 msec, procedure in accordance with ISO 13320-1 and the information in the technical manual and specifications from the instrument manufacturer; result given in % by vol.
6. Particle size determination by laser diffraction with wet dispersal: Master-sizer 2000 with Hydro 2000SM wet-dispersion unit (Malvern Instruments Ltd., UK); dispersion medium low-viscosity silicone oil (manufacturer: Evonik Goldschmidt GmbH, Germany; manufacturer's name: Tegiloxan3, manufacturer's article no.: 9000305); dispersant RI: 1.403; stirrer speed: 2500 rpm; tray type: general purpose; background time: 7500 msec; measurement time: 7500 msec; obscuration limits: 7.0-13.0%; procedure in accordance with ISO 13320-1 and the information in the technical manual and specifications from the instrument manufacturer; result given in % by vol.
   Procedure: the suspension cell is filled with the low-viscosity silicone oil, the sample is added in portions until the target obscuration range (7.0-13.0%) has been reached, and the measurement is started after a waiting time of 2 minutes.
   Particle Size Determination:
   by dry sieving via a sieve tower: Retsch AS 200 control, Retsch (Germany); amount of substance: about 110.00 g; sieving time: 30 minutes; amplitude intensity: 1 mm; interval: 5 seconds; analytical sieve with metal-wire fabric in accordance with DIN ISO 3310; mesh widths (in µm): 710, 600, 500, 400, 355, 300, 250, 200, 150, 100, 75, 50, 32; amount distribution per sieve fraction indicated in the tables as "% by weight of the sample weight":
7. The tabletting tests are carried out as follows:
   The mixtures in accordance with the compositions indicated in the experimental part are mixed for 5 minutes in a sealed stainless-steel container (capacity: about 2 l, height: about 19.5 cm, diameter: about 12 cm outside dimension) in a laboratory tumble mixer (Turbula T2A, Willy A. Bachofen, Switzerland).
   The magnesium stearate employed is Parteck LUB MST (vegetable magnesium stearate) EMPROVE exp Ph. Eur., BP, JP, NF, FCC Article No. 1.00663 (Merck KGaA, Germany) which has been passed through a 250 µm sieve.
   The compression to give 500 mg tablets (11 mm punch, round, flat, with bevel edge) is carried out in a Korsch EK 0-DMS instrumented eccentric tabletting machine (Korsch, Germany) with the Catman 5.0 evaluation system (Hottinger Baldwin Messtechnik—HBM, Germany).
   Depending on the pressing force tested (nominal settings: ~5, ~10, ~20 and ~30 kN; the effectively measured actual pressing forces are indicated in the examples), at least 100 tablets are produced for evaluation of the pressing data and the pharmaceutical formulation characteristic numbers.
Tablet hardnesses, diameters and heights: Erweka Multicheck 5.1 (Erweka, Germany); average data (arithmetic means) from in each case 20 tablet measurements per pressing force. The measurements are carried out one day after the tablet production.
Tablet abrasion: TA420 friability tester (Erweka, Germany); instrument parameters and performance of the measurements in accordance with Ph. Eur. 7th Edition "Friability of Uncoated Tablets". The measurements are carried out one day after tablet production.
Tablet weight: Multicheck 5.1 (Erweka, Germany) with Sartorius CPA 64 balance (Sartorius, Germany). Quoting of the average value (arithmetic mean) from the weighing of 20 tablets per pressing force. The measurements are carried out one day after tablet production.
Characterisation of the Materials Used
1. PVA Grades Used and their Properties:
1.1 Raw Materials for Grinding
1.1.1. PVA 26-88: Polyvinyl Alcohol 26-88, Suitable for Use as Excipient EMPROVE® exp Ph. Eur., USP, JPE, Article No. 1.41352, Merck KGaA, Darmstadt, Germany
1.1.2. PVA 40-88: polyvinyl alcohol 40-88, suitable for use as excipient EMPROVE® exp Ph. Eur., USP, JPE, Article No. 1.41353, Merck KGaA, Darmstadt, Germany
   These PVA grades are in the form of coarse particles with a size of several millimetres which cannot be employed in this form as a directly compressible tabletting matrix.

The coarse particles do not allow reproducible filling of the dies and thus also do not allow a constant tablet weight at the high rotational speeds of the (rotary) tableting machines. In addition, only fine-grained PVAs are able to ensure homogeneous distribution of the active compound in the tablet—without the occurrence of separation effects; this is absolutely necessary for ensuring individual dosage accuracy of the active compound (content uniformity) in each tablet produced. In addition, only a fine-grained PVA can also ensure the homogeneous gel formation throughout the tablet body that is necessary for reproducible retardation.

For these reasons, the above-mentioned coarse-grained PVA grades must be comminuted, i.e. ground, before use as directly compressible retardation matrices.

In order to determine the optimum particle size or particle-size distribution of the two PVA grades with respect to their compressibility, in each case 3 particle fractions of different particle size were produced by cold grinding.

1.2 Ground PVA Grades 1.2.1. Ground PVA 26-88, from Polyvinyl Alcohol 26-88 Article No. 1.41352
having the average particle-size fractions Dv50 (laser diffraction; dry dispersal)
Fraction 1: Dv50 84.88-87.60 μm
Fraction 2: Dv50 120.28-123.16 μm
Fraction 3: Dv50 206.86-224.48 μm 1.2.2. Ground PVA 40-88, from polyvinyl alcohol 40-88 Article No. 1.41353
having the average particle-size fractions Dv50 (laser diffraction; dry dispersal)
Fraction 1: Dv50 85.84-87.37 μm
Fraction 2: Dv50 115.97-120.52 μm
Fraction 3: Dv50 206.83-211.55 μm Grinding:

The grinding of the PVA grades is carried out in an Aeroplex 200 AS spiral jet mill from Hosokawa Alpine, Augsburg, Germany, under liquid nitrogen as cold grinding in a temperature range from 0° C. to minus 30° C. The different particle fractions are produced empirically, in particular by variation of the grinding temperature, i.e. the grinding conditions are varied by on-going in-process controls of the particle size until the desired particle size fraction is obtained.

The resultant product properties of the ground PVA grades, in particular the powder characteristics, such as bulk density, tapped density, angle of repose, BET surface area, BET pore volume and the particle size distributions, are evident from the following tables:

Bulk Density, Tapped Density, Angle of Repose, BET Surface Area, BET Pore Volume:

(details on the measurement methods, see under Methods)

| Sample | Bulk density (g/ml) | Tapped density (g/ml) | Angle of repose (°) |
|---|---|---|---|
| PVA 26-88* 1st fraction | 0.51 | 0.70 | 36.7 |
| PVA 26-88* 2nd fraction | 0.54 | 0.72 | 34.2 |
| PVA 26-88* 3rd fraction | 0.57 | 0.74 | 35.2 |
| PVA 40-88* 1st fraction | 0.51 | 0.70 | 34.0 |
| PVA 40-88* 2nd fraction | 0.53 | 0.71 | 35.0 |
| PVA 40-88* 3rd fraction | 0.56 | 0.72 | 33.8 |

*ground PVA

| Sample | BET surface area (m$^2$/g) | BET pore volume (cm$^3$/g) |
|---|---|---|
| PVA 26-88* 1st fraction | 0.35 | 0.0019 |
| PVA 26-88* 2nd fraction | 0.26 | 0.0015 |
| PVA 26-88* 3rd fraction | 0.20 | 0.0011 |
| PVA 40-88* 1st fraction | 0.33 | 0.0018 |
| PVA 40-88* 2nd fraction | 0.22 | 0.0016 |
| PVA 40-88* 3rd fraction | 0.19 | 0.0011 |

*ground PVA

Particle Distribution Determined by Laser Diffraction with Dry Dispersal (1 Bar Counterpressure):

Figures in μm (details on the measurement method, see under Methods)

| Sample | Dv5 | Dv10 | Dv20 | Dv25 | Dv30 | Dv50 | Dv75 | Dv90 | Dv95 |
|---|---|---|---|---|---|---|---|---|---|
| PVA 26-88* 1st fraction | 17.39 | 24.78 | 38.52 | 45.59 | 52.97 | 87.60 | 161.70 | 285.80 | 526.73 |
| PVA 26-88* 2nd fraction | 22.81 | 33.47 | 53.87 | 64.26 | 74.92 | 123.16 | 213.12 | 320.40 | 394.31 |
| PVA 26-88* 3rd fraction | 34.27 | 51.46 | 85.84 | 104.56 | 124.33 | 210.80 | 350.73 | 499.99 | 593.56 |
| PVA 40-88* 1st fraction | 16.33 | 23.54 | 37.10 | 44.13 | 51.49 | 85.96 | 156.09 | 245.33 | 304.05 |
| PVA 40-88* 2nd fraction | 21.56 | 31.96 | 51.45 | 61.20 | 71.15 | 115.97 | 200.37 | 299.76 | 364.57 |
| PVA 40-88* 2nd fraction | 37.50 | 56.52 | 92.13 | 110.24 | 128.68 | 206.83 | 334.62 | 472.78 | 559.87 |

*ground PVA

Particle Distribution Determined by Laser Diffraction with Dry Dispersal (2 Bar Counterpressure):

Figures in μm (details on the measurement method, see under Methods)

| Sample | Dv5 | Dv10 | Dv20 | Dv25 | Dv30 | Dv50 | Dv75 | Dv90 | Dv95 |
|---|---|---|---|---|---|---|---|---|---|
| PVA 26-88* 1st fraction | 16.15 | 23.53 | 37.22 | 44.26 | 51.56 | 85.05 | 151.30 | 240.02 | 305.79 |
| PVA 26-88* 2nd fraction | 21.04 | 31.58 | 52.06 | 62.54 | 73.32 | 122.08 | 213.33 | 320.49 | 390.77 |
| PVA 26-88* 3rd fraction | 31.97 | 48.56 | 81.95 | 100.26 | 119.78 | 206.86 | 350.52 | 508.72 | 613.02 |
| PVA 40-88* 1st fraction | 15.46 | 22.54 | 36.12 | 43.27 | 50.77 | 85.84 | 156.51 | 247.86 | 309.84 |
| PVA 40-88* 2nd fraction | 20.84 | 31.22 | 51.29 | 61.57 | 72.13 | 120.52 | 215.62 | 344.29 | 457.95 |
| PVA 40-88* 3rd fraction | 36.99 | 55.90 | 92.07 | 110.69 | 129.66 | 209.09 | 336.49 | 472.11 | 556.60 |

*ground PVA

Particle Distribution Determined by Laser Diffraction with Dry Dispersal (3 Bar Counterpressure):

Figures in μm (details on the measurement method, see under Methods)

| Sample | Dv5 | Dv10 | Dv20 | Dv25 | Dv30 | Dv50 | Dv75 | Dv90 | Dv95 |
|---|---|---|---|---|---|---|---|---|---|
| PVA 26-88* 1st fraction | 15.99 | 23.44 | 37.29 | 44.35 | 51.65 | 84.88 | 150.53 | 237.38 | 299.34 |
| PVA 26-88* 2nd fraction | 20.77 | 31.28 | 51.54 | 61.82 | 72.37 | 120.28 | 210.97 | 317.50 | 386.93 |
| PVA 26-88* 3rd fraction | 33.68 | 52.28 | 90.41 | 111.23 | 132.97 | 224.48 | 367.96 | 518.55 | 611.79 |
| PVA 40-88* 1st fraction | 15.50 | 22.86 | 36.99 | 44.35 | 52.00 | 87.37 | 158.92 | 250.34 | 310.78 |
| PVA 40-88* 2nd fraction | 20.62 | 31.15 | 51.23 | 61.23 | 71.61 | 117.75 | 203.67 | 303.91 | 368.85 |
| PVA 40-88* 3rd fraction | 37.26 | 56.18 | 92.22 | 110.98 | 130.24 | 211.55 | 340.76 | 475.48 | 558.34 |

*ground PVA

Particle Distribution Determined by Tower Sieving:

Figures in percent by weight (details on the measurement method, see under Methods)

| Sample | <32 μm | 32-50 μm | 50-75 μm | 75-100 μm | 100-150 μm | 150-200 μm | 200-250 μm |
|---|---|---|---|---|---|---|---|
| PVA 26-88* 1st fraction | 1.8 | 15.2 | 16.1 | 18.2 | 23.1 | 12.0 | 5.7 |
| PVA 26-88* 2nd fraction | 3.8 | 7.7 | 13.2 | 14.6 | 20.8 | 16.9 | 10.1 |
| PVA 26-88* 3rd fraction | 0.5 | 5.2 | 7.4 | 10.0 | 15.7 | 12.8 | 14.1 |
| PVA 40-88* 1st fraction | 2.2 | 14.9 | 16.9 | 17.6 | 20.0 | 13.6 | 6.5 |
| PVA 40-88* 2nd fraction | 1.0 | 12.8 | 14.6 | 15.9 | 21.9 | 14.5 | 8.6 |
| PVA 40-88* 3rd fraction | 0.8 | 2.3 | 6.4 | 9.7 | 15.2 | 14.2 | 15.5 |

| Sample | 250-300 μm | 300-355 μm | 355-400 μm | 400-500 μm | 500-600 μm | 600-710 μm | >710 μm |
|---|---|---|---|---|---|---|---|
| PVA 26-88* 1st fraction | 2.5 | 1.7 | 1.1 | 1.0 | 0.6 | 0.6 | 0.4 |
| PVA 26-88* 2nd fraction | 4.9 | 3.1 | 1.8 | 2.0 | 0.4 | 0.4 | 0.3 |
| PVA 26-88* 3rd fraction | 9.7 | 8.3 | 5.0 | 8.9 | 1.8 | 0.4 | 0.2 |
| PVA 40-88* 1st fraction | 3.0 | 2.0 | 1.1 | 1.1 | 0.8 | 0.2 | 0.1 |

-continued

| | | | | | | | |
|---|---|---|---|---|---|---|---|
| PVA 40-88* 2nd fraction | 4.1 | 2.5 | 1.4 | 1.6 | 0.4 | 0.5 | 0.2 |
| PVA 40-88* 3rd fraction | 11.8 | 9.5 | 5.0 | 7.9 | 1.4 | 0.2 | 0.1 |

*ground PVA

2. Microcrystalline Celluloses (MCCs)
2.1 Vivapur® Type 200, microcrystalline cellulose, Ph. Eur., NF, JP, JRS Pharma, Rosenberg, Germany
2.2 Vivapur® Type 102 Premium, microcrystalline cellulose, Ph. Eur., NF, JP, JRS Pharma, Rosenberg, Germany Particle Distribution Determined by Laser Diffraction with Dry Dispersal (1 Bar Counterpressure):
Figures in µm (details on the measurement method, see under Methods)

| Sample | Dv10 | Dv20 | Dv25 | Dv30 | Dv50 | Dv75 | Dv90 |
|---|---|---|---|---|---|---|---|
| Vivapur ® 102 | 31.56 | 53.04 | 66.00 | 79.89 | 135.87 | 215.53 | 293.94 |
| Vivapur ® 200 | 49.25 | 97.09 | 125.64 | 152.47 | 245.21 | 375.17 | 507.15 |

Particle Distribution Determined by Laser Diffraction with Dry Dispersal (2 Bar Counterpressure):
Figures in µm (details on the measurement method, see under Methods)

| Sample | Dv10 | Dv20 | Dv25 | Dv30 | Dv50 | Dv75 | Dv90 |
|---|---|---|---|---|---|---|---|
| Vivapur ® 102 | 27.55 | 45.97 | 57.41 | 70.40 | 127.29 | 208.92 | 288.93 |
| Vivapur ® 200 | 44.08 | 86.21 | 113.63 | 140.90 | 235.62 | 365.86 | 497.34 |

Particle Distribution Determined by Laser Diffraction with Dry Dispersal (3 Bar Counterpressure):
Figures in µm (details on the measurement method, see under Methods)

| Sample | Dv10 | Dv20 | Dv25 | Dv30 | Dv50 | Dv75 | Dv90 |
|---|---|---|---|---|---|---|---|
| Vivapur ® 102 | 23.61 | 38.84 | 48.19 | 59.22 | 114.76 | 198.37 | 278.99 |
| Vivapur ® 200 | 38.43 | 73.36 | 97.85 | 124.94 | 223.50 | 356.46 | 490.73 |

Particle Distribution Determined by Laser Diffraction with Wet Dispersal (in Low-Viscosity Silicone Oil):
Figures in µm (details on the measurement method, see under Methods)

| Sample | Dv10 | Dv20 | Dv25 | Dv30 | Dv50 | Dv75 | Dv90 |
|---|---|---|---|---|---|---|---|
| Vivapur ® 102 | 28.28 | 47.27 | 58.07 | 69.46 | 119.03 | 200.35 | 285.42 |
| Vivapur ® 200 | 33.53 | 59.12 | 74.18 | 90.77 | 171.42 | 302.56 | 434.89 |

3. Other Materials
3.1 Parteck LUB MST (vegetable magnesium stearate) EMPROVE exp Ph. Eur., BP, JP, NF,
FCC Article No. 1.00663 (Merck KGaA, Germany)
3.2 Colloidal silicon dioxide, highly disperse suitable for use as excipient
EMPROVE exp Ph. Eur., NF, JP, E 551 Article No. 1.13126 (Merck KGaA, Germany)

Experimental Results

The following experiments have shown that the particle size of the PVA used has a considerable influence on the pressing behaviour (pressing force/tablet hardness ratio).

A) Result:
It was found that co-mixtures based on ground polyvinyl alcohols having a Dv50 of 70-90 µm have particularly good compressibility compared with coarser PVA particle-size fractions in combination with microcrystalline celluloses (MCCs). Thus, in Example A1, tablet hardnesses of >400 N are obtained at a pressing force of 20 kN and even harnesses of >500 N are obtained at a pressing force of 30 kN. In Example A3 too, tablet hardnesses of >350 N (at a pressing force of 20 kN) or >450 N (at a pressing force of 30 kN) are achieved.

These specific PVA/MCC co-mixtures are thus particularly suitable in direct tableting as matrices for the formulation of retard tablets in combination with active compounds which are poorly compressible per se.

B) Procedure:
1. Preparation of the blends consisting of the two commercial microcrystalline celluloses with the respective PVA particle-size fractions in the mixing ratio 1:1.
2. After mixing for 5 minutes in a Turbula mixer, 0.25% by weight of highly disperse silicon dioxide are added, and the mixture is mixed again for 5 minutes. The mixture is then passed through an 800 µm hand sieve.
3. After addition of 0.25% by weight of Parteck® LUB MST, the mixture is mixed again for 5 minutes and subsequently compressed.
4. The tablet characterisation is carried out with respect to the parameters tablet hardness, tablet weight, tablet height, tablet abrasion and requisite ejection force.

C) Experimental Results:

1a. Preparation of the Blends of the Microcrystalline Cellulose Vivapur® 102 Premium with the 3 Particle-Size Fractions of PVA 26-88 and PVA 40-88

General description: the respective particle-size fractions of PVA 26-88 and PVA 40-88 are passed through an 800 μm hand sieve in order to remove any coarse components and agglomerates. 300 g of this sieved product are weighed out into a 2 l Turbula mixing vessel, 300 g of the microcrystalline cellulose Vivapur® 102 Premium are added, and the mixture is mixed for 5 min. in a T2A Turbula mixer.

TABLE 1a

Composition of the co-mixtures of the ground PVA fractions with the microcrystalline cellulose Vivapur 102 Premium

| Composition | 50% by weight of PVA | 50% by weight of MCC |
|---|---|---|
| Example A1 | PVA 26-88* 1st fraction | Vivapur ® 102 Premium |
| Comparison B1 | PVA 26-88* 2nd fraction | Vivapur ® 102 Premium |
| Comparison C1 | PVA 26-88* 3rd fraction | Vivapur ® 102 Premium |
| Example A2 | PVA 40-88* 1st fraction | Vivapur ® 102 Premium |
| Comparison B2 | PVA 40-88* 2nd fraction | Vivapur ® 102 Premium |
| Comparison C2 | PVA 40-88* 3rd fraction | Vivapur ® 102 Premium |

*ground PVA

1b. Blends with Highly Disperse Silicon Dioxide

In order to improve the flowability, 0.25% by weight of highly disperse silicon dioxide are added to each of the examples and comparisons and mixed again for 5 minutes.

1 c. Compression of these Blends and Tablet Characterisation

Gen. description: 1.25 g of magnesium stearate are added to in each case 498.75 g of the co-mixtures from Examples A1 and A2 and Comparisons B1, C1, B2 and C2 prepared above in a Turbula mixing vessel, the mixture is mixed again for 5 minutes in a T2A Turbula mixer and tableted in a Korsch EK 0-DMS eccentric press.

TABLE 1b

Tableting data of the co-mixtures of the ground PVA fractions with the microcrystalline cellulose Vivapur ® 102 Premium

| Sample | A Nominal | A Actual | B | C | D | E | F |
|---|---|---|---|---|---|---|---|
| Example A1 | 5 | 5.3 | 104.8 | 501.4 | 5.6 | 0.05 | 113.8 |
|  | 10 | 9.8 | 226.8 | 503.8 | 4.9 | 0 | 114.0 |
|  | 20 | 19.9 | 465.2 | 506.1 | 4.5 | 0 | 66.1 |
|  | 30 | 29.7 | 593.5 | 505.2 | 4.4 | 0 | 50.0 |
| Comparison B1 | 5 | 5.0 | 75.6 | 496.1 | 5.6 | 0.13 | 104.4 |
|  | 10 | 9.9 | 177.9 | 495.3 | 4.9 | 0 | 109.3 |
|  | 20 | 20.9 | 372.6 | 496.8 | 4.5 | 0 | 67.3 |
|  | 30 | 29.8 | 459.6 | 497.6 | 4.4 | 0 | 55.4 |
| Comparison C1 | 5 | 4.9 | 55.6 | 499.6 | 5.5 | 0.25 | 108.7 |
|  | 10 | 10.6 | 144.6 | 500.8 | 4.8 | 0 | 116.2 |
|  | 20 | 19.8 | 278.0 | 500.2 | 4.5 | 0 | 84.3 |
|  | 30 | 30.7 | 388.5 | 498.2 | 4.3 | 0 | 68.0 |
| Example A2 | 5 | 5.0 | 92.4 | 497.7 | 5.5 | 0.05 | 111.9 |
|  | 10 | 9.5 | 207.2 | 496.7 | 4.8 | 0 | 118.6 |
|  | 20 | 20.9 | 447.7 | 498.7 | 4.3 | 0 | 68.4 |
|  | 30 | 28.0 | 544.4 | 500.3 | 4.3 | 0 | 55.3 |
| Comparison B2 | 5 | 5.2 | 80.3 | 497.8 | 5.7 | 0.04 | 117.9 |
|  | 10 | 9.3 | 171.7 | 499.6 | 5.1 | 0 | 126.4 |
|  | 20 | 18.7 | 360.7 | 502.1 | 4.6 | 0 | 85.6 |
|  | 30 | 28.4 | 495.4 | 507.0 | 4.6 | 0 | 63.9 |
| Comparison C2 | 5 | 5.4 | 53.7 | 502.5 | 5.7 | 0.28 | 104.1 |
|  | 10 | 9.9 | 119.2 | 502.6 | 5.1 | 0 | 114.4 |
|  | 20 | 19.6 | 255.4 | 497.3 | 4.6 | 0 | 84.4 |
|  | 30 | 27.1 | 326.8 | 496.7 | 4.5 | 0 | 71.5 |

Key:
A: Pressing force [kN]
B: Tablet hardness after 1 day [N]
C: Tablet weight [mg]
D: Tablet height [mm]
E: Abrasion [%]
F: Ejection force (N)

FIG. 1 shows a graph of the very different pressing force/tablet hardness profiles for better illustration.

2a. Preparation of the Blends of the Microcrystalline Cellulose Vivapur® 200 with the 3 Particle-Size Fractions of PVA 26-88 and PVA 40-88

General description: the respective particle-size fractions of PVA 26-88 and PVA 40-88 are passed through an 800 μm hand sieve in order to remove any coarse components and agglomerates. 300 g of this sieved product are weighed out into a 2 l Turbula mixing vessel, 300 g of the microcrystalline cellulose Vivapur® 200 are added, and the mixture is mixed for 5 min. in a T2A Turbula mixer.

TABLE 2a

Composition of the co-mixtures of the around PVA fractions with the microcrystalline cellulose Vivapur ® 200

| Composition | 50% by weight of PVA | 50% by weight of MCC |
|---|---|---|
| Example A3 | PVA 26-88* 1st fraction | Vivapur ® 200 |
| Comparison B3 | PVA 26-88* 2nd fraction | Vivapur ® 200 |
| Comparison C3 | PVA 26-88* 3rd fraction | Vivapur ® 200 |
| Example A4 | PVA 40-88* 1st fraction | Vivapur ® 200 |
| Comparison B4 | PVA 40-88* 2nd fraction | Vivapur ® 200 |
| Comparison C4 | PVA 40-88* 3rd fraction | Vivapur ® 200 |

*ground PVA

2b. Blends with Highly Disperse Silicon Dioxide

In order to improve the flowability, 0.25% by weight of highly disperse silicon dioxide are added to each of the examples and comparisons and mixed again for 5 minutes.

2c. Compression of these Blends and Tablet Characterisation

Gen. description: 1.25 g of magnesium stearate are added to in each case 498.75 g of the co-mixtures from Examples A3 and A4 and Comparisons B3, C3, B4 and C4 prepared above in a Turbula mixing vessel, the mixture is mixed again for 5 minutes in a T2A Turbula mixer and tableted in a Korsch EK 0-DMS eccentric press.

TABLE 2b

Tableting data of the co-mixtures of the ground PVA fractions with the microcrystalline cellulose Vivapur ® 200

| Sample | A Nominal | A Actual | B | C | D | E | F |
|---|---|---|---|---|---|---|---|
| Example A3 | 5 | 5.1 | 72.7 | 494.3 | 5.6 | 0.19 | 108.1 |
|  | 10 | 10.0 | 183.5 | 493.5 | 4.9 | 0 | 115.7 |
|  | 20 | 19.9 | 387.8 | 495.8 | 4.5 | 0 | 74.4 |
|  | 30 | 29.6 | 507.8 | 494.2 | 4.3 | 0 | 59.1 |

TABLE 2b-continued

Tableting data of the co-mixtures of the ground PVA fractions with the microcrystalline cellulose Vivapur ® 200

| Sample | A Nominal | A Actual | B | C | D | E | F |
|---|---|---|---|---|---|---|---|
| Comparison B3 | 5 | 5.0 | 58.0 | 500.4 | 5.6 | 0.27 | 102.2 |
| | 10 | 9.9 | 145.0 | 500.2 | 5.0 | 0 | 109.6 |
| | 20 | 20.2 | 309.1 | 501.4 | 4.5 | 0 | 72.7 |
| | 30 | 29.7 | 416.6 | 502.5 | 4.5 | 0 | 60.6 |
| Comparison C3 | 5 | 5.0 | 39.7 | 495.6 | 5.5 | 1.53 | 98.6 |
| | 10 | 10.1 | 100.3 | 495.6 | 4.9 | 0.01 | 109.2 |
| | 20 | 20.9 | 211.4 | 497.8 | 4.5 | 0 | 79.0 |
| | 30 | 30.1 | 295.4 | 497.6 | 4.4 | 0 | 68.2 |
| Example A4 | 5 | 5.0 | 70.1 | 498.9 | 5.5 | 0.27 | 108.7 |
| | 10 | 9.8 | 179.6 | 499.8 | 4.8 | 0 | 119.3 |
| | 20 | 20.9 | 391.4 | 501.6 | 4.4 | 0 | 75.8 |
| | 30 | 29.5 | 491.6 | 503.1 | 4.3 | 0 | 62.9 |
| Comparison B4 | 5 | 5.1 | 53.2 | 497.0 | 5.7 | 0.42 | 105.8 |
| | 10 | 10.0 | 138.7 | 498.0 | 5.0 | 0.01 | 118.6 |
| | 20 | 18.8 | 281.7 | 493.6 | 4.6 | 0 | 82.4 |
| | 30 | 29.1 | 389.4 | 491.1 | 4.5 | 0 | 64.9 |
| Comparison C4 | 5 | 5.3 | 35.5 | 498.7 | 5.7 | 1.96 | 92.3 |
| | 10 | 10.2 | 87.8 | 501.1 | 5.1 | 0 | 103.0 |
| | 20 | 19.3 | 176.7 | 502.6 | 4.7 | 0 | 80.7 |
| | 30 | 28.5 | 242.2 | 502.9 | 4.6 | 0 | 67.4 |

Key:
A: Pressing force [kN]
B: Tablet hardness after 1 day [N]
C: Tablet weight [mg]
D: Tablet height [mm]
E: Abrasion [%]
F: Ejection force (N)

Figure 2:
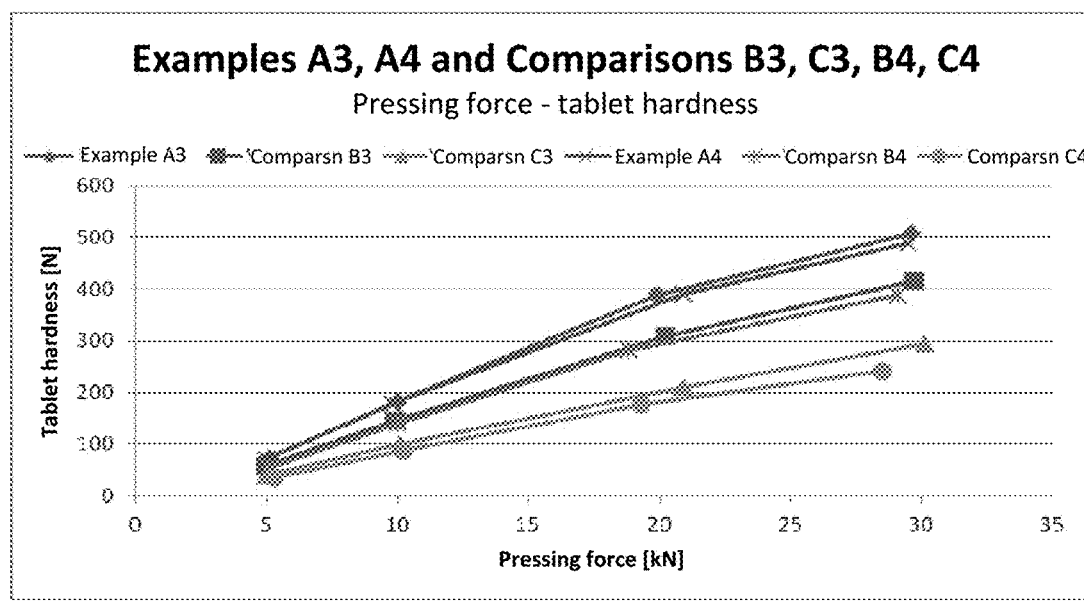

FIG. 2 shows a graph of the very different pressing force/tablet hardness profiles for better illustration.

The invention claimed is:

1. A premix, consisting of a co-mixture of polyvinyl alcohols (PVAs) which have average particle sizes <100 µm, and microcrystalline celluloses (MCCs) which have an average particle size of ≤150 µm, wherein the co-mixture contains only said polyvinyl alcohols (PVAs) and said microcrystalline celluloses (MCCs);
which co-mixture is of microcrystalline celluloses (MCCs) and polyvinyl alcohols (PVAs) of grades 18-88 and/or 26-88 which are suitable for active compound retardation in accordance with the requirements of the pharmacopoeias Ph. Eur., USP/NF and JPE, and/or of grade 20-99 in accordance with the requirements of JPE and Ph. Eur.; and
wherein the premix is suitable for the production of a directly compressible delayed release active compound-containing tablet, but wherein the premix does not contain an active compound.

2. The premix according to claim 1, wherein the microcrystalline celluloses have an average particle size in the range from 100 µm to 140 µm.

3. The premix according to claim 1, wherein the polyvinyl alcohols have an average particle size in the range from 80 µm to 90 µm.

4. The premix according to claim 1, wherein the polyvinyl alcohols to microcrystalline celluloses have a ratio of 2:1 to 1:2 by weight.

5. The premix according to claim 1, which is a co-mixture of microcrystalline celluloses (MCCs) and polyvinyl alcohols (PVAs) of grade 20-99 in accordance with the requirements of JPE and Ph. Eur.

6. The premix according to claim 1, which is a co-mixture of microcrystalline celluloses (MCCs) and polyvinyl alcohols (PVAs) of grades 18-88 and/or 26-88 which are suitable for active compound retardation in accordance with the requirements of the pharmacopoeias Ph. Eur., USP/NF and JPE.

7. The premix according to claim 1, which is a co-mixture of microcrystalline celluloses (MCCs) and polyvinyl alcohols (PVAs) of grade PVA 26-88 which are suitable for active compound retardation.

8. The premix according to claim 1, which is capable of being shaped by compression at a pressing force of 20 kN to give tablets having hardnesses of >380 N, and which have a friability ≤0.1% by weight.

9. The premix according to claim 1, which is capable of being shaped by compression at a pressing force of 10 kN to give tablets having hardnesses of >178 N, and which have a friability ≤0.1% by weight.

10. The premix according to claim 1, wherein the PVA has been milled or ground at a temperature in the range of 0 to minus 30° C.

11. The premix according to claim 10, wherein the microcrystalline celluloses have an average particle size in the range from 100 µm to 140 µm.

12. The premix according to claim 10, wherein the polyvinyl alcohols have an average particle size in the range from 80 µm to 90 µm.

13. The premix according to claim 10, wherein the polyvinyl alcohols to microcrystalline celluloses have a ratio of 2:1 to 1:2 by weight.

14. The premix according to claim 10, which is a co-mixture of microcrystalline celluloses (MCCs) and polyvinyl alcohols (PVAs) of grade 20-99 in accordance with the requirements of JPE and Ph. Eur.

15. The premix according to claim 10, which is a co-mixture of microcrystalline celluloses (MCCs) and polyvinyl alcohols (PVAs) of grades 18-88 and/or 26-88 which are suitable for active compound retardation in accordance with the requirements of the pharmacopoeias Ph. Eur., USP/NF and JPE.

16. The premix according to claim 10, which is a co-mixture of microcrystalline celluloses (MCCs) and polyvinyl alcohols (PVAs) of grade PVA 26-88 which are suitable for active compound retardation.

17. The premix according to claim 10, which is capable of being shaped by compression at a pressing force of 20 kN to give tablets having hardnesses of >380 N, and which have a friability 0.1% by weight.

18. The premix according to claim 10, which is capable of being shaped by compression at a pressing force of 10 kN to give tablets having hardnesses of >178 N, and which have a friability 0.1% by weight.

19. The premix according to claim 1, wherein the polyvinyl alcohols (PVAs) have not undergone prior granulation.

* * * * *